United States Patent
Volonte' et al.

(12) 
(10) Patent No.: US 6,326,370 B1
(45) Date of Patent: Dec. 4, 2001

(54) USE OF AGONISTS OR ANTAGONISTS OF $P_2$ PURINOCEPTORS FOR THE PREVENTION OF GLUTAMATE-EVOKED CYTOTOXICITY

(75) Inventors: Cinzia Volonte'; Daniela Merlo, both of Rome (IT)

(73) Assignee: Consiglio Nazionale Delle Recerche, Rom (IT)

( * ) Notice: Subject to any disclaimer, the term of this patent is extended or adjusted under 35 U.S.C. 154(b) by 0 days.

(21) Appl. No.: 09/000,403

(22) PCT Filed: Jul. 24, 1996

(86) PCT No.: PCT/EP96/03254

§ 371 Date: Mar. 18, 1998

§ 102(e) Date: Mar. 18, 1998

(87) PCT Pub. No.: WO97/04760

PCT Pub. Date: Feb. 13, 1997

(30) Foreign Application Priority Data

Jul. 28, 1995 (IT) .............................................. MI95A1649

(51) Int. Cl.[7] .................................................... A61K 31/53
(52) U.S. Cl. .............................................................. 514/245
(58) Field of Search .............................................. 514/245

(56) References Cited

FOREIGN PATENT DOCUMENTS 42 30 493    3/1994   (DE) .

OTHER PUBLICATIONS

Driessen et al, Chemical Abstracts, vol. 122, abstract No. 24400, 1994.*
K. Nakazawa Et Al., Naunyn Sckmiedebergs Arch. Pharmacol. vol. 351, n° ²1995 pp. 202–208.
R. Ciccarelli Et Al., J. Neuroshi Res. vol. 39, No. 5, 1994 pp. 556–566.
L. Motin Et Al. ,Br. J. Pharmacol. vol. 115, No. 7, 1995 pp. 1276–1280.
S.J. Pollack Et Al., Neuroshi Lett., vol. 197, No. 3, 1995, pp. 211–214.
V.J. Balcar Et Al., Neuroreport, vol. 7, No. 1, 1995 pp. 69–72.
Hollmann M., Heinemann S., Annu. Rev. Neuroshi vol. 17, pp. 31–108, 1994.
Watkins J.C., Collingridge G.L., "The NMDA receptor" IRL Oxford, 1989.
Bliss T.V.P., Collingridge G.L., "Nature" vol. 361, pp. 31–39, 1993.
Appel S.H., Trends Neuroshi, vol. 16, pp. 3–5, 1993.

* cited by examiner

*Primary Examiner*—William R. A. Jarvis
(74) *Attorney, Agent, or Firm*—Collard & Roe, P.C.

(57) ABSTRACT

This invention relates to the use of agonists or antagonists of $P_2$ purinoceptors for the prevention of glutamate-evoked cytotoxicity and in particular use of Basilen Blue D-3G (Reactive Blue 2), Cibacron Blue 3GA and 5-adenylylimidodiphosphate (AMPPNP). In the presence of cytotoxic concentrations of glutamate, these compounds sustain cellular survival of central nervous system (CNS) neurons, such as for example postnatal rat cerebellar granule neurons.

8 Claims, 8 Drawing Sheets

USE OF AGONISTS OR ANTAGONISTS OF P$_2$ PURINOCEPTORS FOR THE PREVENTION OF GLUTAMATE-EVOKED CYTOTOXICITY

This application is a 371 of PCT/EP96/03254, filed Jul. 24, 1996.

BACKGROUND OF THE INVENTION

The present invention relates to the use of a specific class of compounds for the prevention of glutamate-evoked cytotoxicity.

STATE OF THE ART

Glutamate constitute the major excitatory neurotransmitter of the central nervous system (Hollmann M., Heinemann S., Annu. Rev. Neurosci. 17, 31–108, 1994) and the ubiquitous distribution of glutamate receptors throughout the CNS proves that glutamate plays a central role in a wide range of physiological as well as pathological events (Watkins J. C., Collingridge G. L., The NMDA receptor, IRL Oxford, 1989).

By most plausible theories and several experimental findings it is suggested a central role for glutamate-dependent neurotransmission in functions such as learning, pattern recognition, and memory (Bliss T. V. P. Collingridge G. L., Nature 361, 31–39, 1993).

It has also been known for decades that glutamate is toxic to neurons in vivo and in culture and that glutamate receptor functioning is crucial in a number of brain diseases and injuries (Appel S. H., Trends Neurosci. 16, 3–5, 1993). Many neurological illnesses involving strokes or epileptic seizures result in fact in brain damage just because of over-stimulation by glutamate, and degenerative diseases among which Alzheimer's, Huntington's, Parkinson's and amyotrophic lateral sclerosis (ALS) involve neuronal cell death caused by excessive activation of the glutamate receptors.

OBJECTS OF THE INVENTION

Object of the present invention is to provide a specific class of compounds for the modulation of glutamate-evoked neurotransmission and neurotoxicity, which allows the possible treatment of acute and chronic neurodegenerative diseases.

Another object of the present invention is to provide a specific class of compounds which allows the modulation of glutamate-related physiological functions, among which pain, hormonal balance, blood pressure, thermoregulation, respiration, learning, pattern recognition and memory.

Still an object of the present invention is to provide a specific class of compounds which can be used as pharmacological tools for the prevention of glutamate-evoked cytotoxicity.

A further object of the present invention is to provide a specific class of compounds which represents a valid pharmacological alternative to previously described compounds, such as competitive and non-competitive glutamate antagonists,, gangliosides and growth factors, for the treatment of acute and chronic glutamate-related neurological diseases.

DESCRIPTION OF THE INVENTION

These and still other objects and related advantages which will be more clearly stressed by the following description are achieved by the use of compounds which are agonists or antagonists of P$_2$ purinoceptors for the prevention of glutamate-evoked cytotoxicity.

The fundamental novelty of this invention is the correlation between glutamate-evoked biological events and P2 purinoceptor modulators (agonists or antagonists). Both glutamate receptors and P2 purinoceptors share in fact the property of being ionotropic as well as metabotropic kinds of receptors.

As an example, we have chosen the compounds Basilen Blue E 3G (also called Reactive Blue 2) and Cibacron Blue 3GA, which are antagonists of P$_2$ purinoceptors. These compounds can be purchased, for example, from Sigma and their molecular structures and main characteristics are described on the 1995 Sigma catalog distributed in Italy, respectively on pages 149 for Basilen Blue E-3G and 266 for Cibacron Blue 3GA. The other compound we have chosen is 5-adenylylimidodiphosphate (AMPPNP), which is an agonist of P2 purinoceptors. This compound can be also purchased from Sigma and its molecular structure and main characteristics are described in page 52 of the Sigma catalog published in Italy in 1995.

Always according to the present invention, these compounds are used to prevent glutamate-evoked cytotoxicity in the nervous system's cells, particularly in CNS neurons. As a cellular model system for CNS neurons we have adopted postnatal rat cerebellar neurons. These cells, which are among the best characterized primary neuronal cultures, when isolated from postnatal rat cerebellum (Lasher R. S., and Zagon I. S., Brain Res. 41, 428–438, 1972), develop in vitro their mature phenotype as interneurons which use glutamate as a neurotransmitter and furthermore constitute an excellent model system for the study of glutamate-mediated cytotoxicity.

By exposing granule neurons to 100 $\mu$M glutamate for 15–30 min is obtained (after 15–20 hours) 80–100% of total cell death. We find that the P$_2$ purinoceptor antagonist basilen blue, also called reactive blue 2 (an anthraquinone sulfonic acid derivative), when somministered to granule neurons at 100 $\mu$M in the simultaneous presence of glutamate, completely sustains cellular survival, thereby abolishing the cytotoxic action of glutamate. The effects of basilen blue on cerebellar granule cell morphology reveal, despite the exposure to glutamate, which otherwise induces complete cell death, apparently healty-looking cell bodies that do bear a dense network of highly branching processes. Adhesion and neurites fasciculation are also preserved by basilen blue. The acute response characterized by rapid swelling of the cell body and loss of brightness, generally observed in granule neurons within the first 5 min of treatment with glutamate, is furthermore prevented by addition of basilen blue, suggesting that the compound probably acts very early in the chain of events immediately downstream of the EAA-receptor interaction.

It is important to stress that basilen blue per se, up to the highest concentration tested of 300 $\mu$M, is not toxic to the cells and, when somministered to granule neurons for 0.5–26 hours, does not affect plasma membrane permeability (as measured by ethidium bromide uptake), or cellular metabolism (as measured by conversion of MTT into formazan by mitochondrial dehydrogenase activities). Basilen blue prevents glutamate-evoked cell death with an IC50 in the 10–20 $\mu$M range, value generally in agreement with the concentrations of the compound reported for P2 purinoceptor antagonism. The other commercially available isomer of the sulfonic derivatives of anthraquinone (cibacron blue) is effective in this regard. Caffeine, a P1 purinoceptor antagonist, up to 100 μM does not abolish the cytotoxic action of glutamate.

The effects of basilen blue on protection from cytotoxicity are linear with time and depend on the modality of somministration of the compound. When basilen blue is added to the cells 10 min after glutamate, and then incubated with granule neurons for only 15 min, it protects from cell death 60–70% of the entire neuronal population; if somministered only for the last 5 min of treatment of the cells with glutamate, basilen blue sustains survival of 25–40% of total neurons. When instead it is added 1–2 min or 30 min or 2 hours after exposure of granule neurons to glutamate (and then incubated with the cells for the next 20 hours) basilen blue protects from cell death respectively 55–70%, 30% and 10% of the total neuronal population. When it is added before (not during or after) exposure of granule neurons to glutamate, basilen blue requires a pretreatment of at least 20–25 hours in order to prevent by 70–80% the cytotoxic action of glutamate. Inhibition of aspartate uptake is not obtained as a consequence of these same treatments. Independently from the modality of somministration to granule neurons, the prevention of cytotoxicity induced by basilen blue does not depend on new protein synthesis, since it is insensitive to inhibitors such as actinomycin D (used at 10 μM) or anisomycin (used at 100 μM).

Basilen blue inhibits binding of [$^3$H] ATP to membranes of granule neurons with an IC50 of about 10 μM, that corresponds to the IC50 that prevents glutamate-evoked cytotoxicity. Binding studies with [$^3$H] ATP have been performed also directly with intact cells and basilen blue was shown to be as effective.

We have cultured the cells in the continuous presence (from day 1 but not later than day 2 in vitro) of 100 μM 5-adenylylimidodiphosphate (AMPPNP), a known $P_2$ purinoceptor agonist. Glutamate-induced cytotoxicity is inhibited by approximately 50–60% as a consequence of this treatment. An acute exposure of the cells to 100 μM AMP-PNP (simultaneously with glutamate) is not effective in this regard. The fact that by culturing the neurons in the continuous presence of AMPPNP elicits the same effect caused by an acute exposure to basilen blue supports our hypothesis of a direct involvement of purinoceptors in glutamate-dependent neurotoxicity; it moreover suggests that a phenomenon of desensitization of purinoceptors most likely takes place in cerebellar granule cells.

Since D-[$^3$H] aspartate release has been often used as a measure of the functional state of cerebellar granule neurons cultured in vitro and depolarization- or glutamate-evoked aspartate release is a feature progressively aquired by these cells along with neuronal maturation, we decided to test this parameter to further study the biological effects and possible mechanisms used by basilen blue in the prevention of cell death. We find that basilen blue inhibits glutamate-induced release of [$^3$H] aspartate with an IC50 of about 10 μM. The inhibition is almost complete but does not affect basal release and it occurs when the release is measured for 1 min, for longer times (3, 10 and 25 min) or even in the presence of $Mg^{2+}$. Also a cronic exposure of granule neurons for 8 days to 100 μM AMPPNP inhibits by 70–80% the glutamate-evoked release of [$^3$H] aspartate.

Glutamate-dependent neurotoxicity is often accompanied also in cerebellar granule neurons with increase in intracellular $Ca^{2+}$ via a multistep process. Basilen blue, differently from caffeine, almost completely abolishes glutamate-evoked, but not basal, $Ca^{2+}$ uptake with an IC50 of approximately 10 μM. Also this value is in accordance with the IC50 found for inhibition of ATP binding, cytotoxicity and aspartate release. The basilen blue-dependent inhibition occurs when $Ca^{2+}$ uptake is measured for short (1 min) of for longer times (3, 10, and 25 min). The cronic exposure of granule neurons for 8 days to 100 μM AMPPNP inhibits by 50–70% glutamate-evoked $Ca^{2+}$ influx, similarly to the inhibition of cytotoxicity and aspartate release.

Figure 1:
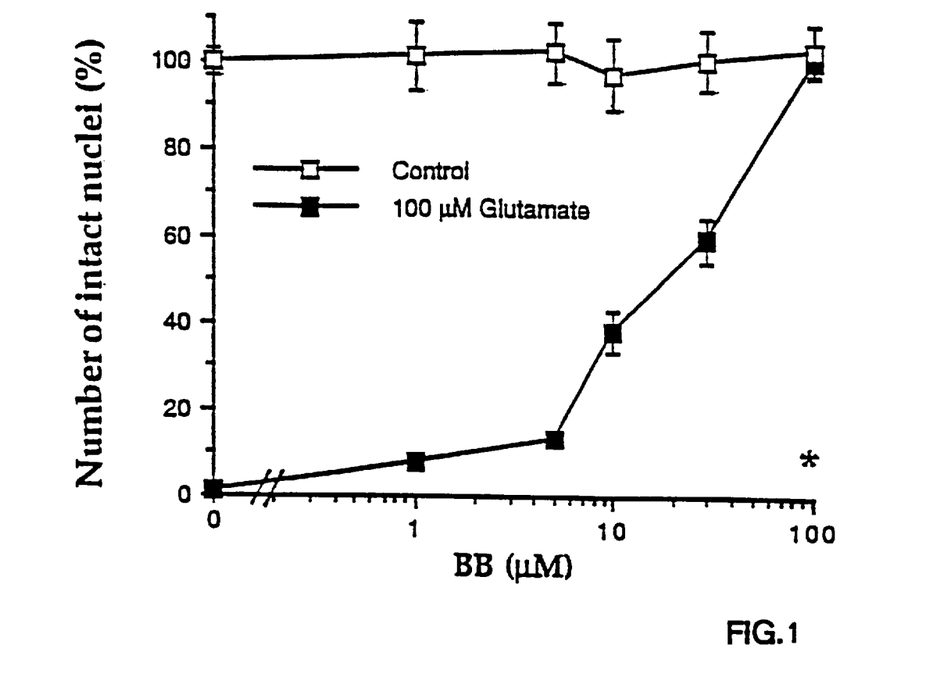
FIG. 1 shows the number of intact nuclei as a function of basilen blue concentration.
Figure 2:
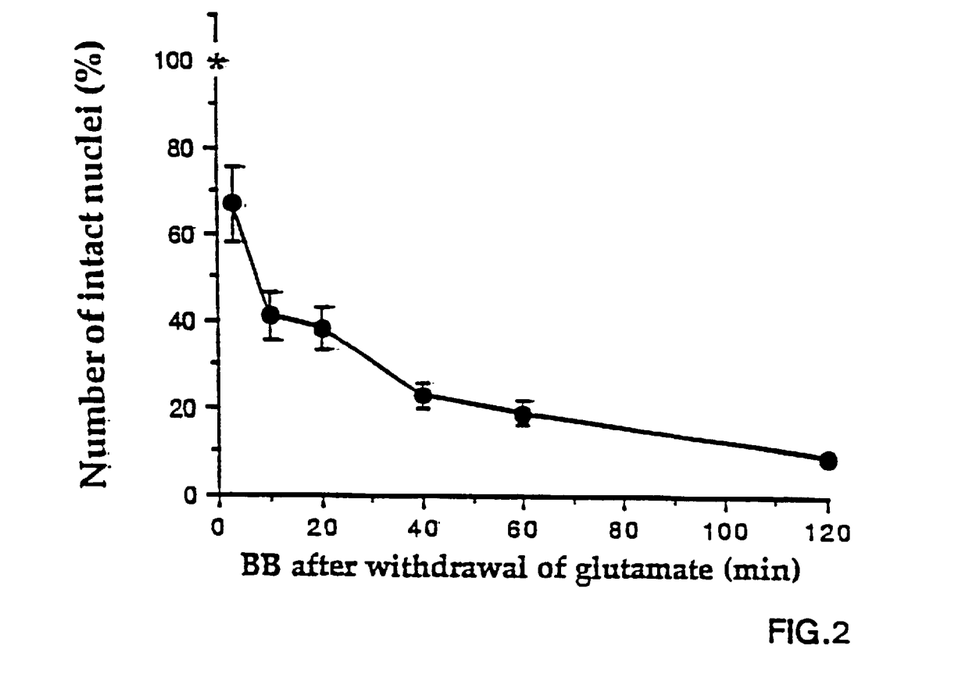
FIG. 2 shows the number of intact nuclei as a function of basilen blue after withdrawal of glutamate.
Figure 3:
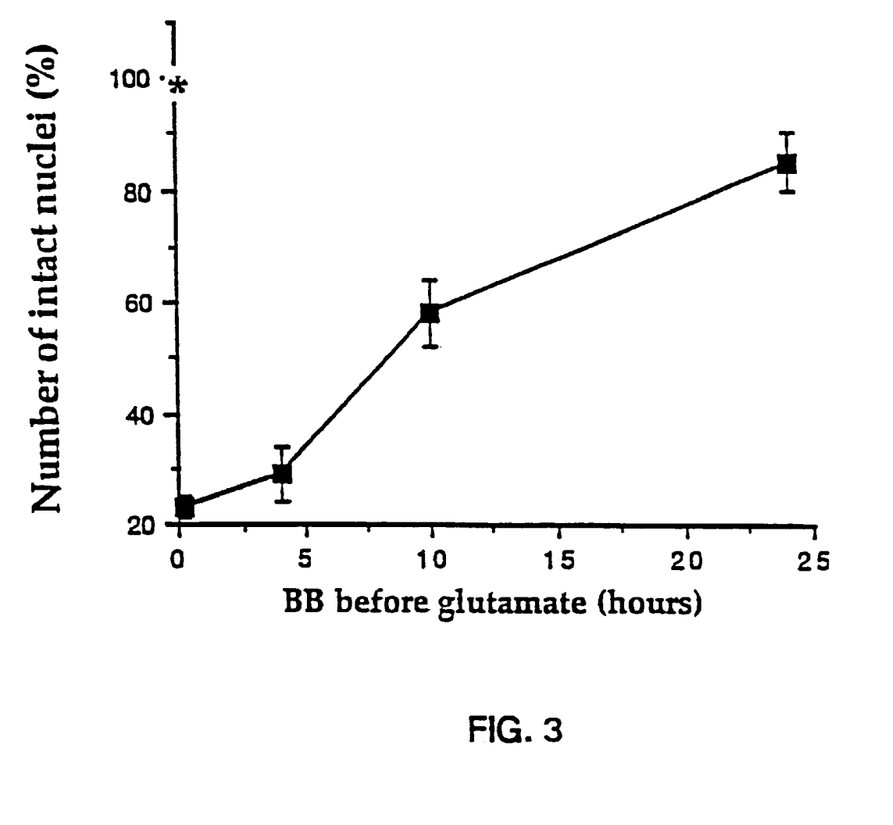
FIG. 3 shows the number of intact nuclei as a function of basilen blue before glutamate.

Basilen Blue prevents cytotoxicity induced by glutamate in cerebellar granule primary cultures: effects of dose-response and modality of addition. Replicate cerebellar granule cultures at 8 DIV were exposed for 25 min to 100 μM glutamate, in the simultaneous presence of different concentrations of basilen blue (FIG. 1). After 20 hours, the cultures were assessed for cell survival by direct count of intact viable nuclei. The asterisk represents the % of nuclei obtained after simultaneous addition to the cells of 100 μM glutamate and 100 μM caffeine. In FIG. 2, replicate cerebellar granule cultures at 8 DIV were exposed for 25 min to 100 μM glutamate. At different time after glutamate withdrawl, basilen blue (100 μM) was added to the medium until the cultures, 20 hours later, were assessed for cell survival by direct count of intact viable nuclei. The asterisk represents the % of nuclei obtained after simultaneous addition to the cells of 100 μM glutamate and 100 μM basilen blue. In FIG. 3, replicate cultures were pretreated in the presence of 100 μM basilen blue for different time, before the addition of 100 μM glutamate for 25 min (performed in the absence of basilen blue). After 20 hours the cultures were assessed for cell survival.

The asterisk represents the % of nuclei obtained after simultaneous addition to the cells of 100 μM glutamate and 100 μM basilen blue. Counts represent means±SEM (n=4) and 100% of cell survival represents 1.75–2×106 total cells.

METHODS. Approximately 20 hours after exposure of granule cells to glutamate, the culture medium was removed and replaced with 1 ml of a detergent-containing lysing solution (0.5% ethyl hexadecyl dimethyl-ammonium bromide, 0.28% acetic acid, 0.5% Triton X-100, 3 mM NaCl, 2 mM $MgCl_2$, in PBS pH 7.4 diluted 1/10).

After 1–2 minutes, the cells were triturated a few times, providing a uniform suspension of single, intact viable nuclei. The latter were quantified by counting in a hemacytometer. Broken or damaged nuclei were not included in the counts.

Figure 4:
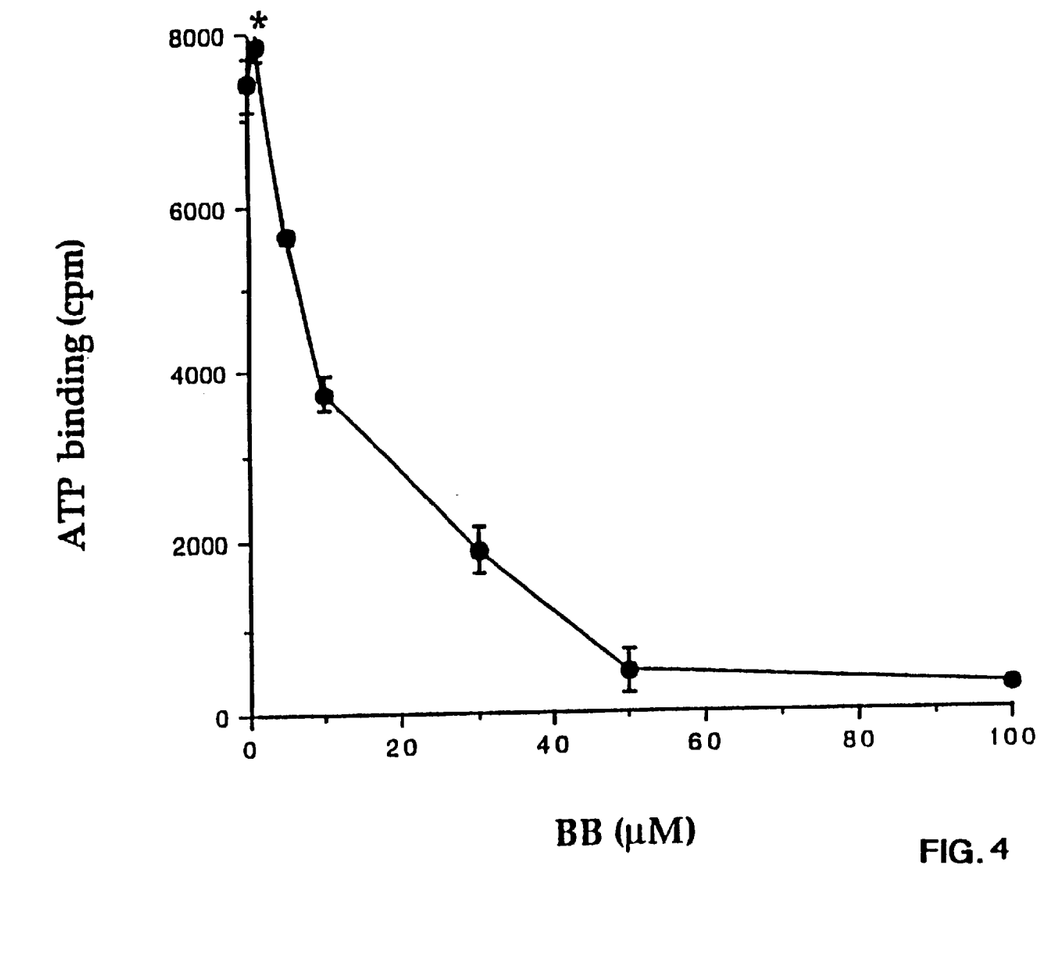
FIG. 4 show the ATP binding as a function of basilen blue concentration.
Figure 5:
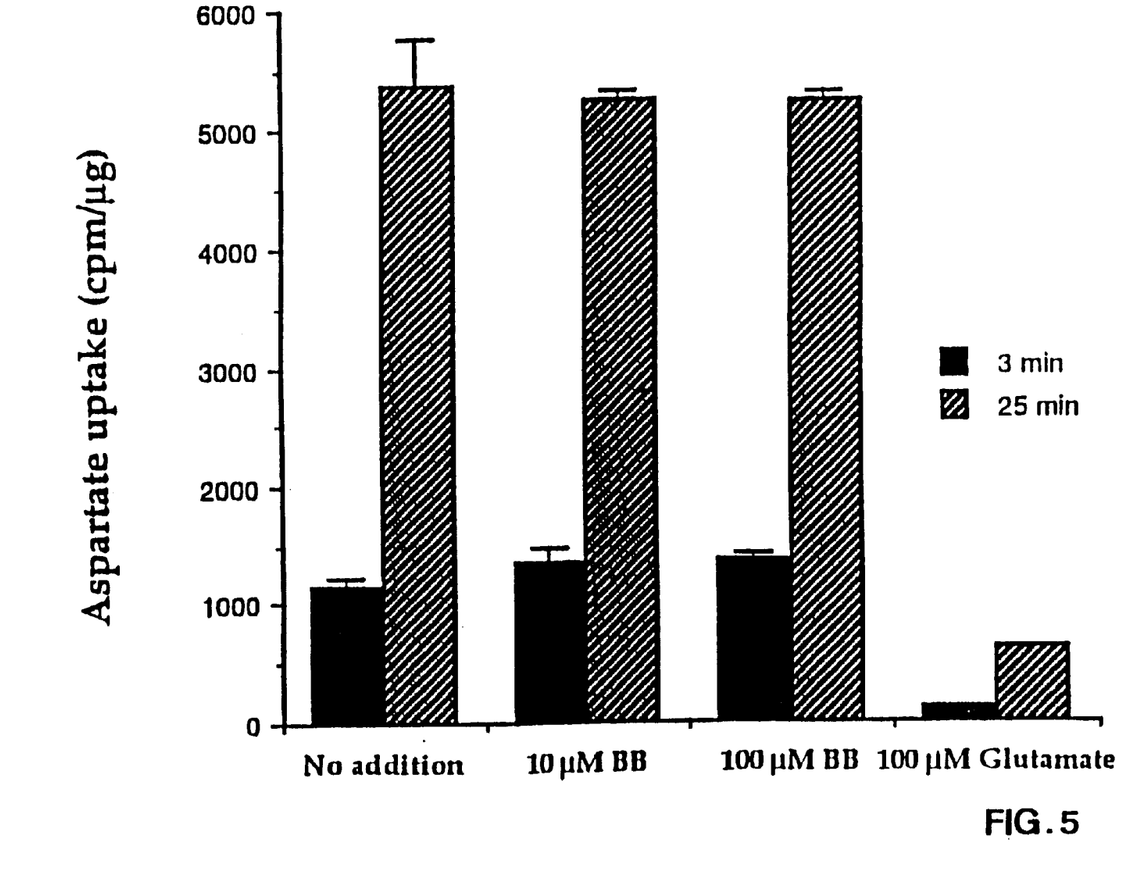
FIG. 5 shows the aspartate uptake as a function of basilen blue concentration.

Basilen Blue inhibits binding of ATP to cerebellar granule cell membranes, but not uptake of aspartate. Membranes were prepared from 8 DIV cerebellar granule ells and 20 $\mu$g of protein were incubated with [$^3$H] ATP (0.5 $\mu$Ci/ml, final concentration 14 nM) (FIG. 4), in the presence of different concentrations of basilen blue, for 1 h at 4° C. Specific binding is shown and counts represent means±SEM (n=3). The asterisk represents the binding performed in the presence of 100 $\mu$M caffeine. In FIG. 5, replicate cerebellar granule cultures at 8 DIV were washed twice and incubated for different times in Locke's solution with [$^3$H] D-2,3 aspartic acid (1 $\mu$Ci/ml, final concentration 40 nM), in the presence of different concentrations of basilen blue. After two washes, cells were dissolved in 0.1 M NaOH and counted for incorporated radioactivity by liquid scintillation counting. Values are shown as cpm/$\mu$g and represent means±SEM (n=3). Protein concentrations were determined by the method of Bradford with ovine serum albumin as standard.

METHODS. Replicate cerebellar granule cells at 8 DIV were collected in ice-cold buffer A (50 mM Tris, 1 mM EGTA, adjusted to pH 7.4 with HCl, containing also 2 mM phenylmethylsulfonyl fluoride, 200 KIU/ml of aprotinin and 1 $\mu$g/ml of leupeptin) and were centrifuged at 35.000×g for 20 min at 4° C. The pellet was resuspended in buffer A to give a protein concentration of 5–6 mg/ml and used immediately for binding studies. After binding with [$^3$H] ATP, the samples (1 ml) were vacuum-filtered through Whatman GF/B glass fiber filters and the filters were immediately washed (3×4 s) with 5 ml of 50 mM Tris-HCl (pH 7.4), air dried and assessed for specifically bound radioactivity by liquid scintillation counting.

Figure 6:
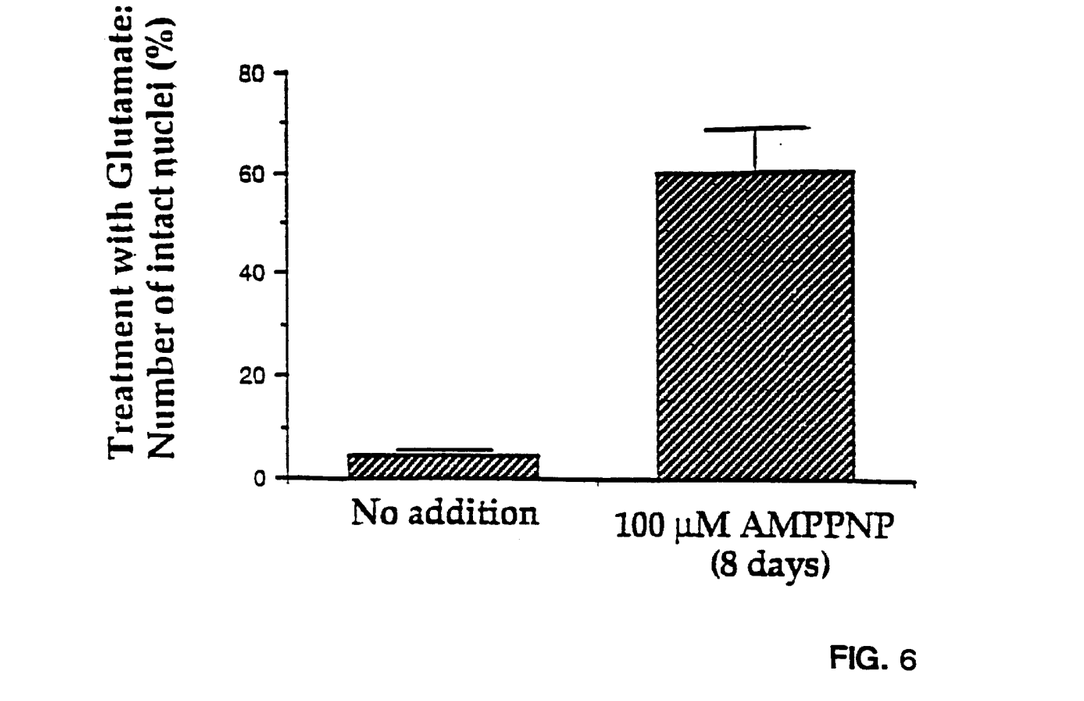
FIG. 6 shows treatment with glutamate and the number of intact nuclei as a function of the addition of AMPPNP.

Culturing cerebellar granule cells in the presence of AMPPNP: modulation of glutamate-dependent cell death, Ca$^{++}$ uptake and aspartate release. Primary cerebellar granule cultures were prepared and starting at 1 DIV some of them were daily supplemented with 100 $\mu$M AMPPNP. (FIG. 6) At 8 DIV, after two washes, some of the cultures were incubated at 20° C. for 25 min with 100 $\mu$M glutamate. The following day, they were assessed for cell survival, as previously described.

Figure 7:
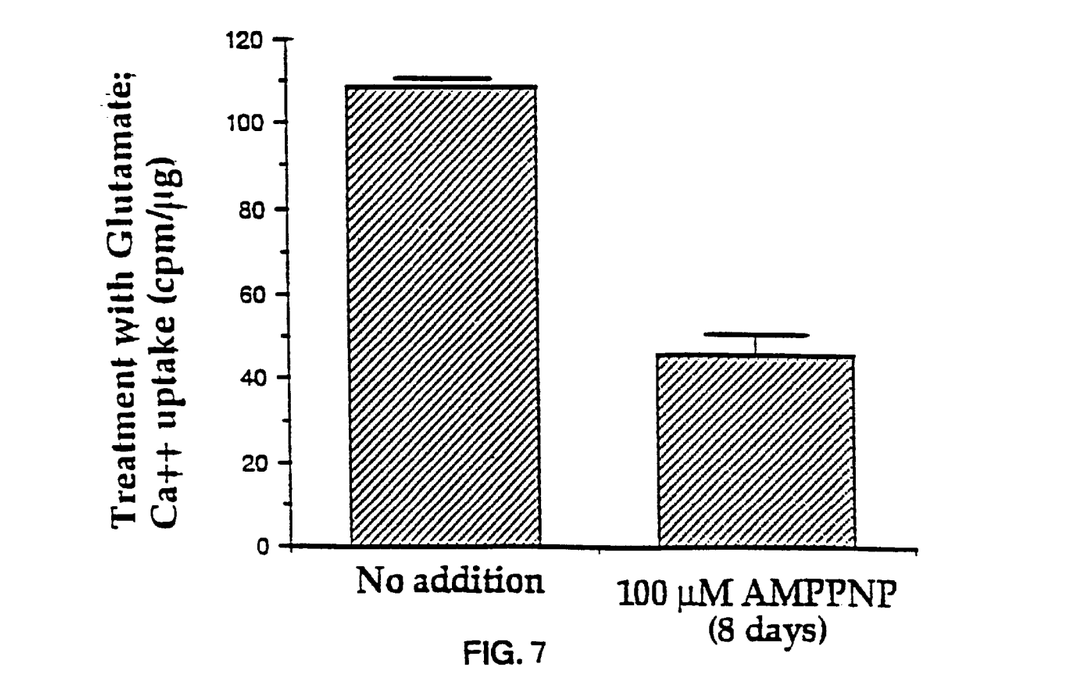
FIG. 7 shows treatment with glutamate and the uptake of calcium as a function of the addition of AMPPNP.
Figure 8:
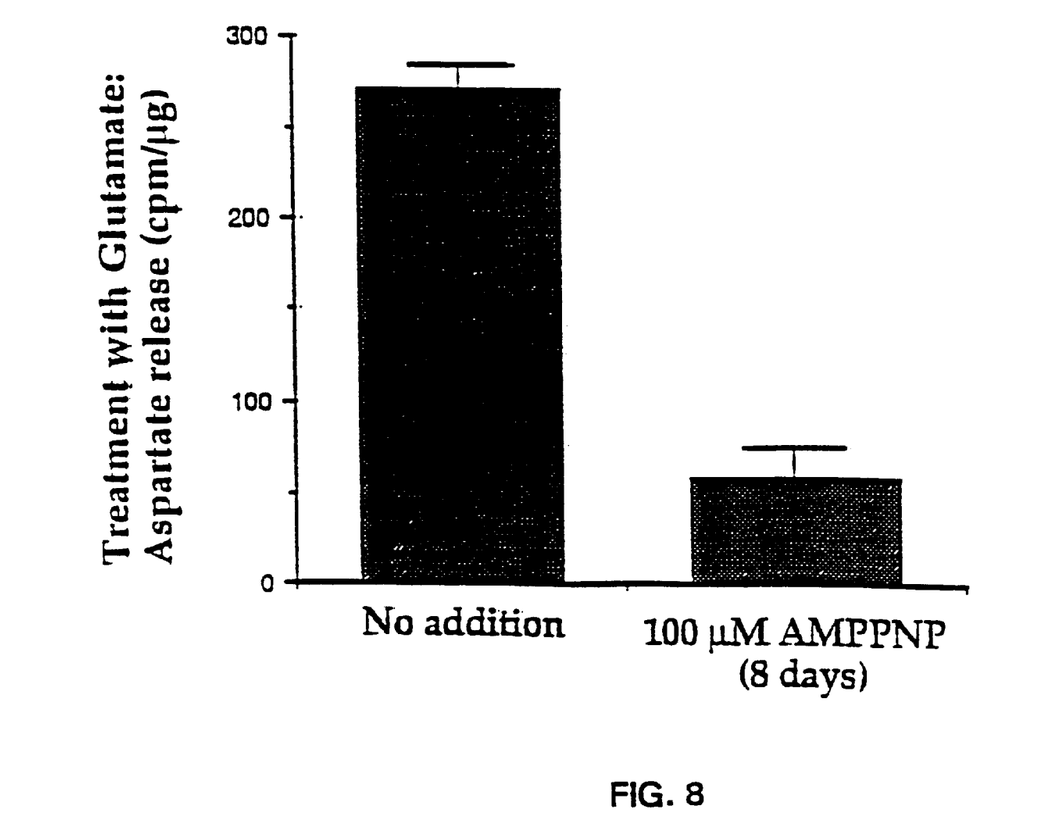
FIG. 8 shows treatment with glutamate and aspartate release as a function of the addition of AMPPNP.

(FIG. 7) Replicate cerebellar granule cultures at 8 DIV were incubated for 1 min in Locke's solution in the presence of 45 Ca$^{++}$ (1 $\mu$Ci/ml), with or without 100 $\mu$M glutamate, and were then assessed for Ca$^{++}$ influx. (FIG. 8) Replicate cerebellar granule cultures at 8 DIV were incubated for 5 min in Locke's solution, in the presence of [$^3$H] D-2,3 aspartic acid (1 $\mu$Ci/ml, final concentration 40 nM) and were then assessed for aspartate release, in the presence or absence of 100 $\mu$M glutamate. Data are expressed as means±SEM (n=3).

Figure 9:
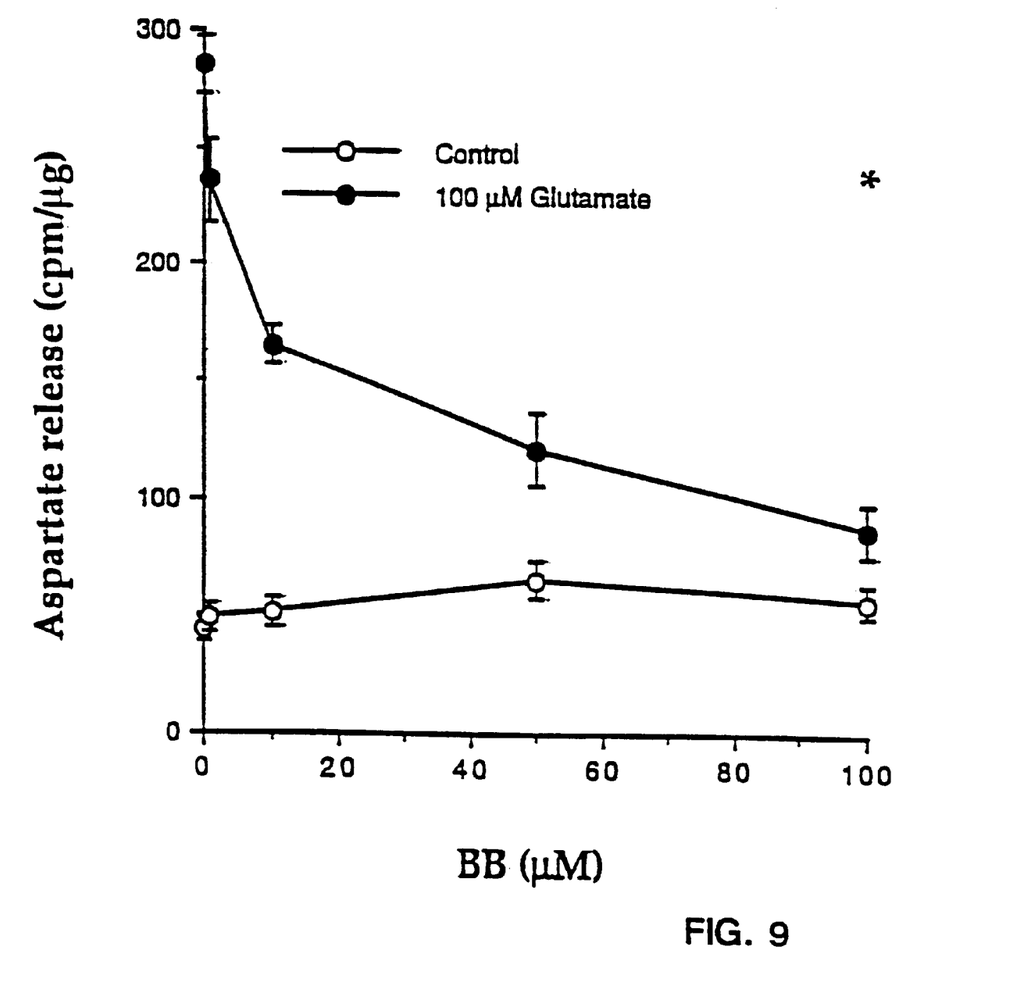
FIG. 9 shows aspartate release as a function of basilen blue concentration.

Basilen Blue inhibits release of aspartate and uptake of Ca$^{++}$ induced by glutamate in cerebellar granule cells. (FIG. 9) Replicate cerebellar granule cultures at 8 DIV were incubated for 5 min in Locke's solution in the presence of [$^3$H] D-2,3 aspartic acid (1 $\mu$Ci/ml, final concentration 40 nM). After two washes, the cultures were then incubated for 1 min in Locke's solution with or without 100 $\mu$M glutamate and in the presence of different concentrations of basilen blue. The buffer removed from the cultures during this release phase was collected into vials and counted for radioactivity. The asterisk represents the release of aspartate obtained in the simultaneous presence of 100 $\mu$M glutamate and 100 $\mu$M caffeine. Cells were dissolved in 0.1 M NaOH and protein concentrations were determined by the method of Bradford, with bovine serum albumin as standard.

Figure 10:
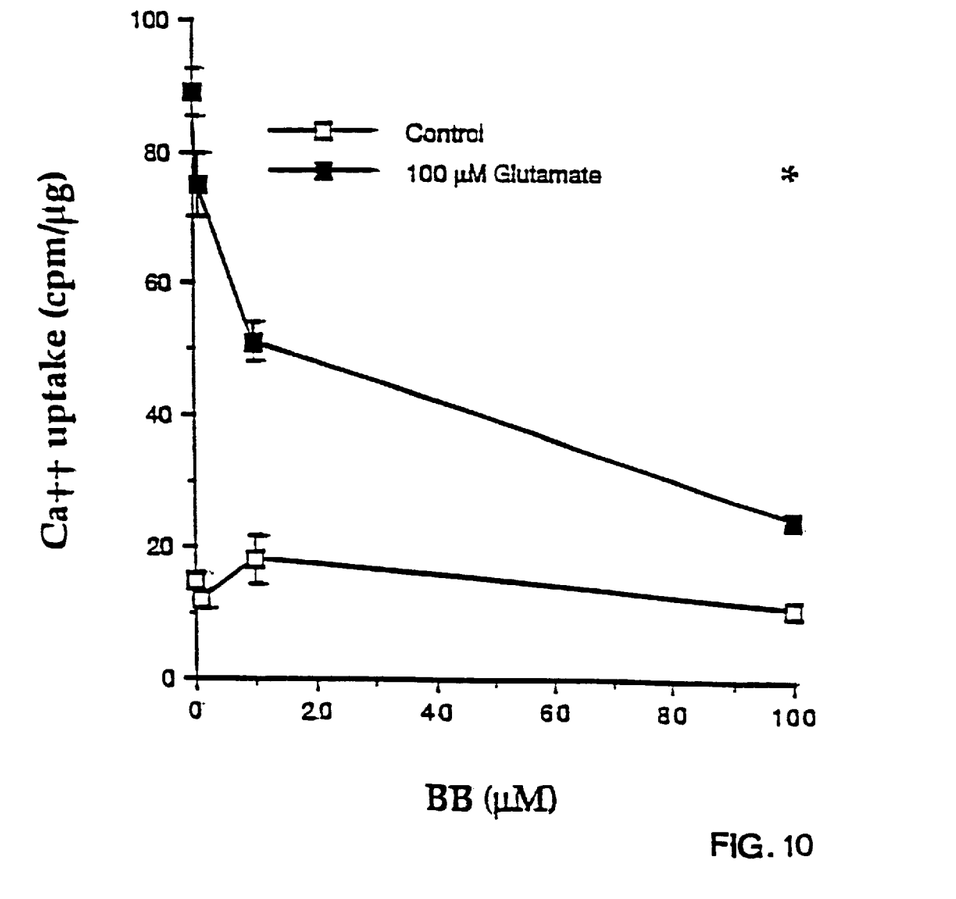
FIG. 10 shows uptake of calcium as a function of basilen blue concentration.

(FIG. 10) Replicate cerebellar granule cultures at 8 DIV were incubated for 1 min in Locke's solution in the presence of 45 Ca$^{++}$ (1 $\mu$Ci/ml), with or without 100 $\mu$M glutamate, and in the simultaneous presence of different concentrations of basilen blue. After two washes with ice-cold 154 mM choline chloride, 2 mM EDTA, the cells were lysed in 0.1 M NaOH and aliquots were collected for measuring Ca$^{++}$ influx (by radioactive counting) and protein concentration. The asterisk represents the Ca$^{++}$ influx obtained in the simultaneous presence of 100 $\mu$M glutamate and 100 $\mu$M caffeine. Data are expressed as means±SEM (n=3).

What is claimed is:

1. A method of preventing glutamate-evoked cytotoxicity in a patient in need thereof comprising
   administering to said patient a therapeutically effective amount of a P$_2$ purinoceptor agonist or antagonist.

2. A method for treating acute and chronic neurodegenerative diseases in a patient in need thereof comprising
   administering to said patient a therapeutically effective amount of a P$_2$ purinoceptor agonist or antagonist.

3. A method of preventing glutamate-evoked neurotoxicity in a patient in need thereof comprising
   administering to said patient a therapeutically effective amount of a pharmacological composition comprising active agent compounds of a P$_2$ purinoceptor agonist or antagonist.

4. The method of preventing glutamate-evoked neurotoxicity according to claim 3,
   wherein said antagonist is selected from the group consisting of Basilen Blue E-3G (Reactive blue 2) and Cibacron Blue 3GA.

5. The method of preventing glutamate-evoked neurotoxicity according to claim 4, wherein said antagonist is Basilen Blue E-3G (Reactive blue 2).

6. A method of treating acute and chronic neurodegenerative diseases in patient in need thereof comprising
   administering to said patient a therapeutically effective amount of a pharmacological composition comprising as active agent compounds a P$_2$ purinoceptor agonist or antagonist.

7. A method of modulating glutamate-evoked physiological functions in a patient in need thereof comprising
   administering to said patient a therapeutically effective amount of a pharmacological composition comprising as active agent compounds a P$_2$ purinoceptor agonist or antagonist.

8. The method of modulating glutamate-evoked physiological functions according to claim 7,
   wherein said glutamate-evoked physiological functions are selected from the group consisting of pain, hormonal balance, blood pressure, thermoregulation, respiration, learning, pattern recognition and memory.

* * * * *